United States Patent [19]

Huettner et al.

[11] 4,232,226
[45] Nov. 4, 1980

[54] DIAGNOSTIC INSTALLATION FOR PRODUCING TOMOGRAPHIC IMAGES

[75] Inventors: Robert Huettner, Heroldsbach; Gerhard Kuetterer; Hartmut Sklebitz, both of Erlangen, all of Fed. Rep. of Germany

[73] Assignee: Siemens Aktiengesellschaft, Berlin & Munich, Fed. Rep. of Germany

[21] Appl. No.: 60,417

[22] Filed: Jul. 25, 1979

[30] Foreign Application Priority Data

Aug. 18, 1978 [DE]  Fed. Rep. of Germany ....... 2836282

[51] Int. Cl.³ .......................... A61B 6/00; A61B 6/02; G21K 1/04
[52] U.S. Cl. .................................. 250/445 T; 250/505
[58] Field of Search ............................. 250/445 T, 505

[56] References Cited

U.S. PATENT DOCUMENTS 4,149,082   4/1979   Haendle et al. .................. 250/445 T

FOREIGN PATENT DOCUMENTS 2722141 12/1978 Fed. Rep. of Germany ....... 250/445 T
2748687  5/1979 Fed. Rep. of Germany ....... 250/445 T

*Primary Examiner*—Alfred E. Smith
*Assistant Examiner*—T. N. Grigsby
*Attorney, Agent, or Firm*—Hill, Van Santen, Steadman, Chiara & Simpson

[57] ABSTRACT

The installation comprises a support table for a patient, a plurality of x-ray sources or similar radiation sources, arranged in a series or planar array, with step-by-step activation of the radiation sources in any desired sequence. The beam of rays and the image field of the image detection installation are shifted in mutually opposite directions, so that sharply defined images are formed of only those details disposed in a specified longitudinal layer of the body as determined by the location of the rotational axis of the beam of rays. In the radiation path of the beam of rays of every radiation source, a beam path control device is arranged for shifting the beam path in relation to a central axis of the radiation source system and of the image pickup system, in dependence upon a laminographic height alteration. For example with plural circular arrays of x-ray sources about the central axis, the beam paths can be jointly adjusted by means of a single motor to intersect at any desired level within the patient receiving region of the support table.

15 Claims, 4 Drawing Figures

DIAGNOSTIC INSTALLATION FOR PRODUCING TOMOGRAPHIC IMAGES

BACKGROUND OF THE INVENTION

The invention relates to a diagnostic installation for producing tomographic images, comprising a support table for a patient, a plurality of x-ray or similar radiation-sources on one side of the support table, arranged in series or in an area array, for the production of a beam of rays, penetrating the patient lying on the support table, and an image detection installation on the other side of the support table, and comprising means for the step-by-step actuation of the radiation sources in any desired sequence, as well as for the purpose of moving the beam of rays and the image field of the image detection installation in mutually opposite directions, so that sharply defined images are formed of only those details disposed in a specified longitudinal layer of the body which is determined by the effective rotational axis of the beam of rays.

X-ray diagnostic installations are known wherein, at the one end of a guide bar, and above the support table, an x-ray tube is mounted, and, at the other end and below the support table, a cassette carrier for a film cassette is mounted. In order to change the direction of the beam of rays, the guide rod can be pivoted about a horizontal axis. In order to provide laminograms, the x-ray tube and the cassette carrier are moved in mutually opposite directions about the pivot axis. As a consequence, sharp images are formed on the film of only details of the particular body layer which is traversed by the pivot axis. Image-formation of all remaining details is more or less strongly blurred. In order to change the laminographic height, the pivot axis can be correspondingly adjusted at the guide bar.

Since the x-ray tube and the cassette carrier are moved in the case of these diagnostic installations, the times required for the preparation of laminographic images are comparatively long.

It has also been proposed (for example in German patent application P 26 47 167 corresponding to U.S. application Ser. No. 837,198 now abandoned), to provide as the radiation source a plurality of x-ray tubes arranged in a surface array, which are actuated in succession in a randomly selectable sequence, and to move the film cassette synchronously with the sequential actuation of the individual tubes. In addition, in order to provide laminograms at a relatively low laminographic angle (zonography), it has been proposed (in German patent application P 27 12 320 corresponding to U.S. application Ser. No. 866,017 now U.S. Pat. No. 4,149,082) to provide, for the purpose of image detection, an x-ray image intensifier with a synchronous deflection device controlled by a control generator.

In the case of the above-cited diagnostic installations, the orientation of the beams of rays emanating from the individual radiation sources present difficulties; in particular the problem arises that the subject to be examined is to be penetrated by the beam of rays at every laminographic height, on the one hand; but the patient is not to be exposed to any unnecessary radiation, on the other hand. It is the object of the present invention to provide a solution to this problem.

SUMMARY OF THE INVENTION

The stated object is achieved in the case of a diagnostic installation of the above-cited type, in accordance with the invention, by virtue of the fact that there is arranged, in the path of rays of the radiation beam of each x-ray source, a beam path control device whose aperture, relative to the central axis of the radiation source and image pickup system, is adjustable.

Advantageous embodiments and further developments of the invention are contained in the subclaims.

An exemplary embodiment of the invention shall be explained in greater detail on the basis of the accompanying sheets of drawings; and other objects, features and advantages will be apparent from this detailed disclosure and from the appended claims.

DETAILED DESCRIPTION

Figure 1:
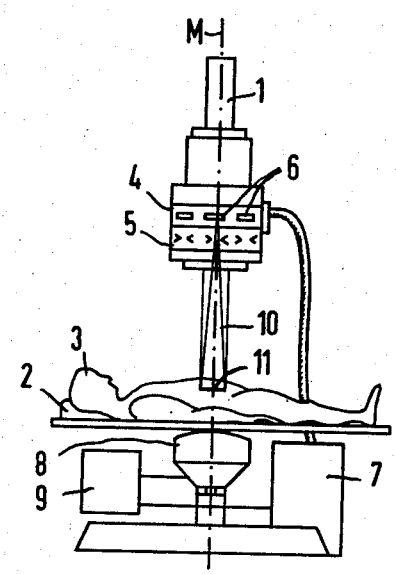
FIG. 1 illustrates an x-ray diagnostic installation in schematic representation.

FIG. 1 illustrates, in a schematic representation, an x-ray diagnostic installation wherein a support table 2 for a patient 3 is supported in a vertically displaceable fashion on a support column 1. Above the patient 3 on the support column 1, an x-ray generator with the tube arrangement 4 and a beam path control arrangement 5 is supported. The tube arrangement 4 contains an array of x-ray tubes 6, concentrically arranged about a center axis M, which x-ray tubes are fed from an electric supply installation 7. Beneath the support table 2, and symmetrically to the center axis M, there is disposed an image intensifier 8, which is connected to an installation referenced by 9, which essentially contains a deflection device synchronized by a control generator, for the image intensifier output image, as well as means for the reproduction of the output image. Emanating from every tube 6 is a cone of rays 10 which, subsequent to traversal of the beam path control arrangement 5, penetrates the patient 3 lying on the support table 2, and produces, on the image intensifier 8, an output image of the subject to be examined in a desired laminographic plane 11 which can be picked up by a television camera and reproduced via a video unit. The output image at the x-ray image intensifier 8 is magnetically deflected by means of two pairs of deflection coils, with the actuation of the deflection coils being effected by means of a deflection device which is synchronized by a control generator. A synchronous image displacement in the image intensifier is thereby achieved analogously to the step-wise switching-on of the x-ray tubes 6. A detailed illustration and explanation of such an installation is described in the German patent application P 27 12 320.0 and in U.S. application Ser. No. 866,017.

Instead of the image intensifier 8 for the purpose of image detection, it is also possible to provide a cassette carrier having a film cassette, which carrier is correspondingly synchronous with and is moved counter to the tube actuation For recording of images in the region (or range) of zonography with a relatively small laminographic angle, however, image reproduction by means of image intensifiers has been proven more advantageous, particularly on account of the extremely low image generation times.

Figure 2:
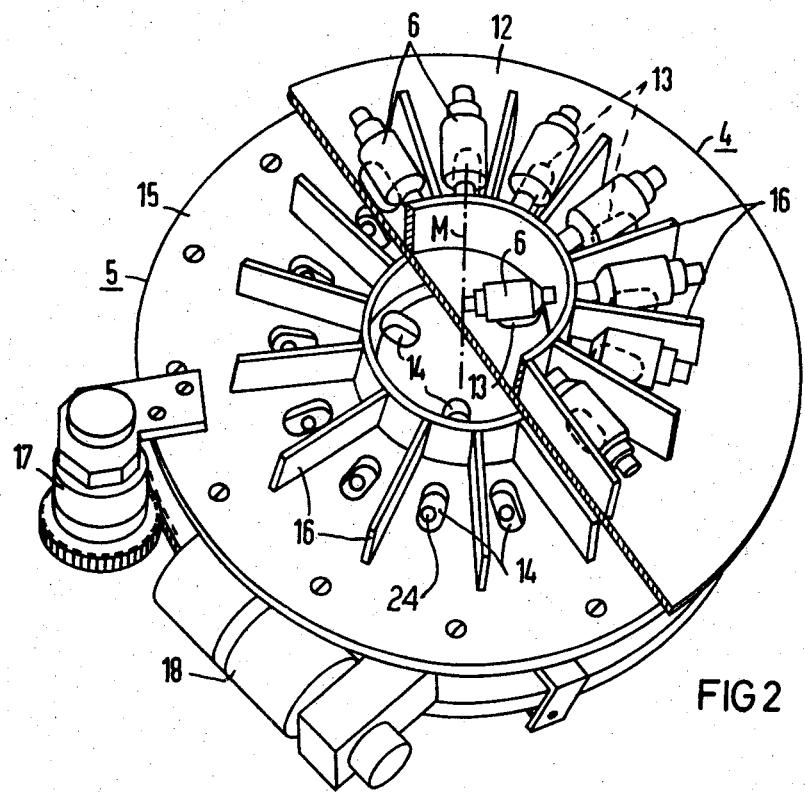
FIG. 2 illustrates the beam path control device and tube arrangement according to FIG. 1, viewed from above, with parts broken away and in section.

FIG. 2 illustrates, in a diagrammatic representation, the tube and beam path control arrangement 4, 5, from above, wherein for the purpose of improved clarity, only a portion of the tube arrangement 4 is illustrated. The x-ray tubes 6 are arranged, uniformly distributed, on a discoid housing section 12; namely, thirteen tubes on an outer circle having approximately one hundred millimeters (100 mm) radius, and three tubes on an inner circle having approximately forty millimeters (40 mm) radius. The housing section 12 manifests, beneath the focal spots of the tubes 6, first stationary oval beam transmitting apertures 13, with which, together with additional stationary, likewise oval openings 14—which are present in a housing section 15 of the beam path control arrangement 5—an initial shaping of the beam (or diaphragming-out) and a protection from undesired stray radiation is achieved. The two housing sections 12 and 15 are arranged parallel to one another at a distance of approximately forty millimeters (40 mm). The respective pairs of cooperating apertures 13 and 14 in the two housing parts 12 and 15 are so arranged that no stray rays from an adjacent source can reach the apertures 14. For the purpose of mutual shielding of rays emanating from the x-ray tubes 6, star-shaped arrangements of shielding partitions 16 are provided disposed between the two housing sections 12 and 15 for partitioning off the respective beam paths, and also above the housing section 12, whereby the tubes 6 are separated from each other. The tubes 6 arranged on the inner circle are disposed axially of the directly corresponding tubes in the outer circle. Reference numerals 17 and 18 designate two adjustment motors for adjusting adjustable beam path control devices to be described in greater detail later, which are arranged beneath the stationary apertures 14.

Figure 3:
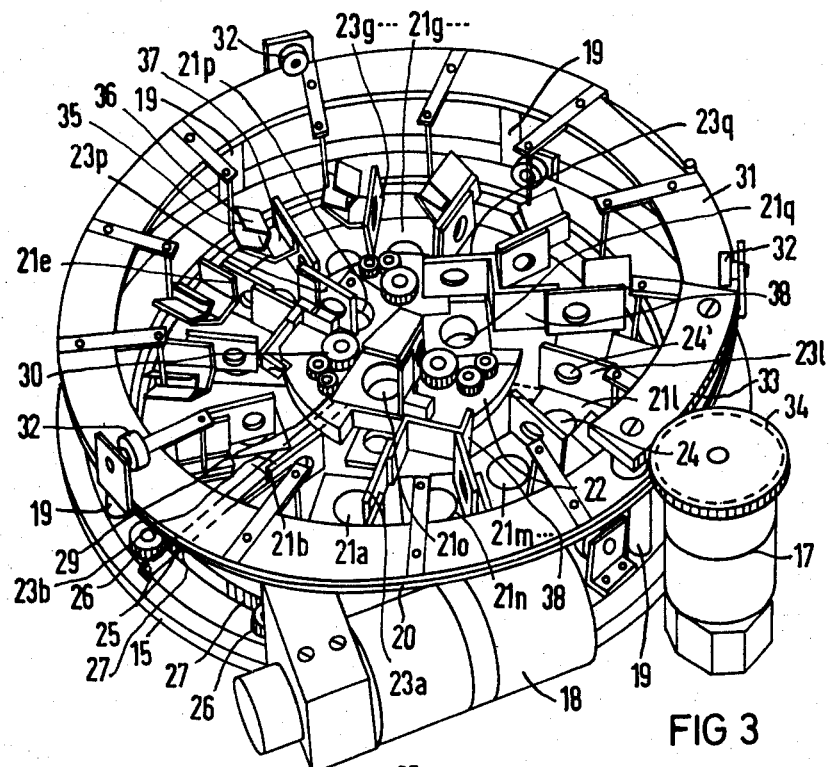
FIGS. 3 and 4 illustrate the beam path control arrangement viewed from below in two different beam path control positions.
Figure 4:
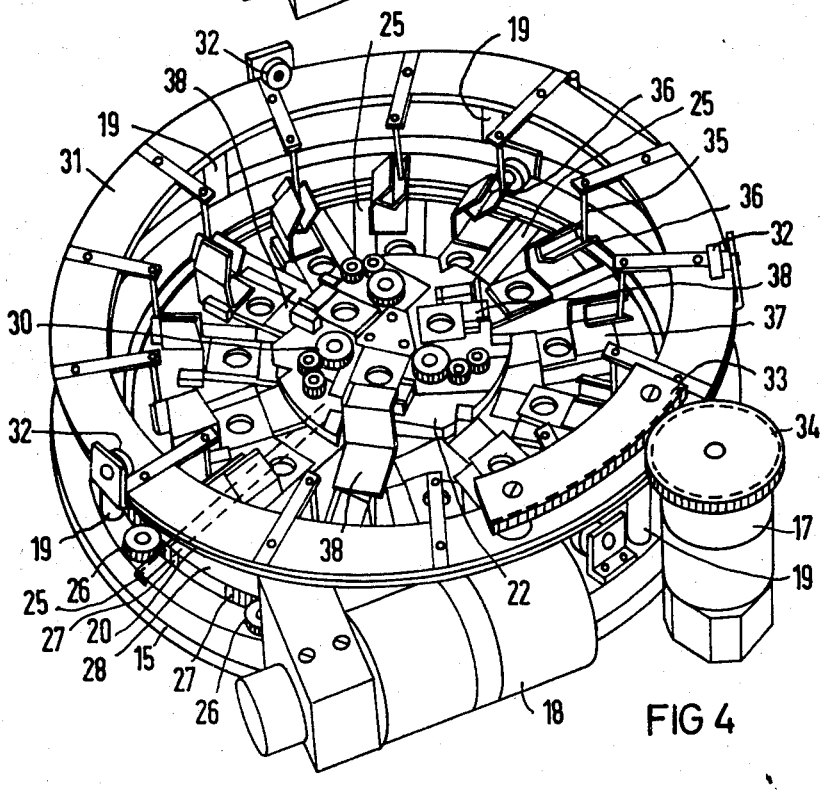

FIGS. 3 and 4 illustrate the underside of the beam path control arrangement 5 and provide a view of the interior of the overall system essentially constructed in the form of a disk.

Section 15, with a plurality of spacing members 19, arranged at the periphery and with an annular frame section 20 mounted thereon, forms the housing in which a total of sixteen apertured diaphragm elements 21a through 21q are supported in a radially displaceable fashion, with a further set of apertured diaphragm elements 21o, 21p, and 21q being displaceably mounted on a plate 22 disposed parallel to the plane of the housing section 15. Associated with the diaphragm elements or beam path control elements 21a through 21q are additional adjustable diaphragm elements 23a through 23q which, in comparison with the apertures 24 of the diaphragm elements 21a–21q, have a smaller aperture 24' (see elements 21l and 23l where the respective apertures 24 and 24' are specifically designated at a "four o'clock position" in FIG. 3). The diaphragm elements 23a–23q are illustrated in FIG. 3 as being folded up (to a non-use position), and in FIG. 4, as being folded down, whereby, in the latter position, the respective diaphragm elements of the set 23a–23q rest on the respective associated diaphragm element of the set 21a–21q, so that the larger aperture cross section of the apertures 24 are restricted by the relatively smaller aperture cross section of apertures 24'.

The diaphragm elements 21a–21q are arranged in star formation in the housing section 15 and are guided so as to be radially mobile. For the purpose of guidance, in a known fashion, a dove-tail groove or the like can be provided. Each of the diaphragm elements 21a–21q, constructed in the form of a small plate, is individually adjustable and is connected to a respective toothed rack 25 which is in engagement with a respective gear wheel 26 (see the "eight o'clock position" in FIGS. 3 and 4). Each gear wheel 26 is rotatably mounted in the housing section 15, and in turn, respectively meshes with an arcuate gear segment 27 at the periphery of a drive ring 28 rotatably mounted above the toothed racks 25 on the housing section 15. The ring 28 has a gear segment which is driven by a motor 18 via a worm gear. Upon rotation of the ring 28 by means of motor 18, the beam path control devices including elements 21a–21q and 23a–23q are adjusted in synchronism via the gear sections 25, 26, depending upon the rotational direction of the motor 18, radially away from the center axis (M in FIG. 1), or radially toward the latter, as a consequence of which the beam path control apertures 24, 24' are moved jointly along the stationary apertures 13, 14, constructed in the form of elongated holes (FIG. 2).

The adjustment of the three beam control elements 21o, 21p and 21q (FIG. 3) proceeds by virtue of the fact that the toothed racks 25, at the outer beam control elements 21b, 21f and 21k are extended such that they project beyond the associated outer beam control elements, respectively, and the free end of each of these toothed racks is in engagement with one of three geared drive shafts 29 (see the "eight o'clock position" in FIG. 3), mounted in the plate 22, which drive shafts 29 finally drive the beam path control elements 21o, 21p and 21q via gears 30 and additional toothed racks. The gears 30 provide a transmission speed ratio of approximately 1:2 from the interior toward the exterior; i.e., the exterior beam path control elements 21a through 21n move, corresponding to the geometric constellation of the beam course, twice as rapidly as the inner beam path control elements 21o, 21p and 21q.

In order to adjust the beam path control elements 23a through 23q with respect to their angular relationship to the respective associated beam path control elements 21a–21q, an adjustment ring 31 is rotatably mounted by means of rollers 32 on the lower stationary annular frame section 20. The drive of the adjustment ring 31 proceeds via a toothed segment 33 which meshes with a gear wheel 34 which is driven by motor 17. At the adjustment ring 31, actuating pins 35, spaced radially toward the interior, are arranged, which are in engagement with U-shaped drivers 36, which, in turn, are fixedly connected via mounting metal sheets 37 with the foldable beam path control elements 23a–23n. The connection of the three beam path control elements 23o, 23p and 23q, disposed in the inner circle, with the corresponding beam path control elements 23a, 23e and 23l, proceeds by means of angles 38 (see FIGS. 3 and 4 at the "four o'clock position"). The actuating pins 35 can slide radially in the respective associated U-shaped driver section 36 if the beam path control elements such as 21b, 23b, (which are fixedly connected with the associated segment 36 for joint radial movement) are moved, with the aid of the drive motor 18, radially toward the exterior, or toward the center axis (M) of the system, respectively.

The radial adjustment of the beam path control devices 21a–21q, 23a–23q proceeds in dependence upon the laminographic plane adjustment; i.e. the adjustment motor 18 is coupled to the laminographic height adjustment installation; namely, in such a manner that, in case of a reduction of the laminographic height, the beam path control devices, corresponding to the geometric constellation of the beams of rays for this laminographic height, are moved radially toward the exterior and away from central axis M. Through this common radial adjustment of the beam path control devices 21a-21q, 23a-23q, an optimum limitation (or restriction) of the cone of rays in dependence upon the adjusted tomographic height is achieved, as a consequence of which a radiation exposure (or dosage) restricted to only that which is necessary, results for the patient.

Through folding-over of the beam control elements 23a-23q onto the beam path control elements 21a-21q, an image format switching-over from a survey (or panoramic) representation (large effective diaphragm aperture) to a detailed representation (small effective diaphragm aperture) with relatively sharply defined contours is achieved.

Instead of the beam path adjustment device illustrated in FIGS. 3 and 4, with toothed racks 25 and gear wheels 26, a structurally simpler adjustment device with a cable drive can also be provided. For such an arrangement, it is proposed that, for every one of the beam path control devices, guided radially in star-formation in corresponding guide elements, and provided with a radially inwardly acting restoring force by means of spring elements, a pulley with two grooves be arranged on the periphery of the beam path control arrangement; for example, on a section corresponding to the housing section 15. In the one groove, a common control cable for all beam path control devices is guided via all pulleys, which control cable is looped about a friction driving pulley with a corresponding elastic force. In the other groove, a drawing cable is guided which is connected with the beam path control device, on the one hand, and, after deflection about the pulley, is connected with the control cable. The connection expediently proceeds by means of a clamping section which is adjustable along the control cable and thus renders possible an adjustment of the individual beam path control devices. The control cable is looped about the friction driving pulley in such a manner that, pursuant to rotation of the friction driving roller alternatively in the one or the other rotational direction, the beam path control apertures 24, 24' are radially adjusted toward the exterior (against the action of the spring elements), or toward the interior (with the aid of the spring elements), respectively.

The related U.S. application Ser. No. 866,017 filed Dec. 30, 1977 has issued as U.S. Pat. No. 4,149,082 dated Apr. 10, 1979.

It will be apparent that many modifications and variations may be effected without departing from the scope of the novel concepts and teachings of the present invention.

We claim as our invention:

1. A diagnostic installation for producing laminographic images, comprising a support table for a patient, a plurality of radiation sources arranged in an array on one side of the support table and each being operable for producing a beam of rays penetrating the patient lying on the support table, and an image detection installation on the other side of the support table, and means for effecting the activation of the radiation sources in a desired sequence, and for controlling the image field of the image detection installation in a coordinated manner so that sharply defined images are formed of only those details disposed at a common layer region where the beams of rays converge and intersect a corresponding longitudinal layer of the body, characterized in that beam path control means (21a-21q) are arranged in every path of rays of the radiation beam (10), of each radiation source (6), said beam path control means having respective shiftable apertures for adjusting the path of each beam of rays relative to an axis (M) of the array of radiation sources to effect a laminographic depth adjustment.

2. A diagnostic installation according to claim 1, characterized in that the radiation sources are arranged in a circular array, and the apertures of the beam path control means are arranged in a corresponding circular array and are radially adjustable to effect the laminographic depth adjustment.

3. A diagnostic installation according to claim 2, characterized in that the radiation sources are arranged on two concentric circles, and the apertures of the beam path control means are arranged in corresponding concentric circles in two planes which are parallel to one another.

4. A diagnostic installation according to claim 1, characterized in that an adjustment device is present for the common adjustment of the beam path control means for all of the radiation sources.

5. A diagnostic installation according to claim 4, characterized in that the beam path control means are guided, in a radially mobile fashion, with the adjustment device comprising a common adjustment drive (18), and gear means (25 through 28) for coupling the common adjustment drive (18) with said beam path control means to jointly shift the apertures thereof radially relative to the axis (M) of the array of radiation sources.

6. A diagnostic installation according to claim 4, characterized in that the adjustment device comprises a driving pulley, driven pulleys for each beam path control means which are arranged in association with the respective beam path control means, a control cable which is common for all beam path control means which is guided about the driven pulleys, and looped under initial tension about the driving pulley, and one drawing cable each leading to every beam path adjustment means for actuating the same in response to actuation of the associated driven pulley via the control cable.

7. Diagnostic installation according to claim 4, characterized in that the adjustment device comprises a rotatably mounted ring means (28), the beam path control means being guided so as to be radially mobile, and the ring means having respective gear segments, and gear means (25 through 27) driven by the respective gear segments for converting the rotational movement of the ring means (28) into a radial movement of the beam path control means.

8. A diagnostic installation according to claim 7, characterized in that every beam path control means has a toothed rack (25) which is in engagement with the gear means for driving of each rack in a generally radial direction in response to rotation of the ring means (28).

9. A diagnostic installation according to claim 8, characterized in that the beam path control means are arranged in an exterior circle at one level and at an inner circle at a different level, toothed racks associated with a number of outer beam path control means (21b, 21f, 21k) in the exterior circle, which correspond to a number of inner beam path control means (21o through 21q) arranged in the inner circle, said toothed racks (25) extending to the inner beam path control means (21o through 21q) arranged in the inner circle, the gear means including gear wheels (30) which are a part of a reduction gear for the purpose of synchronous adjustment of these inner beam path control means (21o through 21q) in relationship to the circle radii.

10. A diagnostic installation according to claim 1, characterized in that guide members are provided for guiding the movement of the beam path control means during adjustment of the laminographic depth, and means providing for individual adjustment of the beam path control means along the respective associated guide member.

11. A diagnostic installation according to claim 1, characterized in that the beam path control means comprises a first device and a second device having different aperture cross sections, and means mounting the first and second devices for relative movement toward and away from each other to vary the effective size of the apertures of the beam path control means.

12. A diagnostic installation according to claim 11, characterized in that the second devices (23) are mounted next to the first devices (21) such that the second devices can be folded over in a hinge-like fashion toward overlying relation to the respective first devices.

13. A diagnostic installation according to claim 12, characterized in that an adjustment ring (31) is present which is rotatably mounted, that the adjustment ring (31) having actuating pins (35) directed inwardly radially relative to the axis (M) of the array of radiation sources, bifurcated drivers (36), which render possible a radial guidance of the pins (35) in response to rotation of the adjustment ring (31) to fold the second devices (23) into overlying relation to the respective first devices (21).

14. An x-ray diagnostic installation according to claim 1, characterized in that, in order to adjust the beam path control means (21, 23), electric adjustment motors (17, 18) are present, which are controlled in dependence upon the desired laminographic depth adjustment.

15. An x-ray diagnostic installation according to claim 1, characterized in that, between the adjustable beam path control means (21, 23) and the radiation sources (6), fixed diaphragm devices (13, 14) are present with apertures having a spacing (a) from one another, and with aperture width which corresponds to the adjustment path of the apertures of the adjustable beam path control means (21, 23).

* * * * *